(12) United States Patent
Paulsen et al.

(10) Patent No.: US 8,343,478 B2
(45) Date of Patent: Jan. 1, 2013

(54) PARAPOXVIRUSES IN COMBINATION WITH OTHER ANTIVIRAL AGENTS FOR THE TREATMENT OF VIRAL DISEASES

(75) Inventors: Daniela Paulsen, Wuppertal (DE); Helga Ruebsamen-Schaeff, Wuppertal (DE); Amar Kureishi, Beijing (CN); Gerhard Hunsmann, Goettingen (DE); Christiane Stahl-Hennig, Goettingen (DE); Andreas Meyerhans, Homburg/Saar (DE); Alexandra Schuetz, Mbeya (TZ); Olaf Weber, Wuelfrath (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 1405 days.

(21) Appl. No.: 11/652,937

(22) Filed: Jan. 11, 2007

(65) Prior Publication Data

US 2010/0255032 A1    Oct. 7, 2010

Related U.S. Application Data

(63) Continuation of application No. PCT/EP2005/007395, filed on Jul. 8, 2005.

(30) Foreign Application Priority Data

Jul. 13, 2004   (EP) ..................... 04016414

(51) Int. Cl.
*A61K 39/155*   (2006.01)
*A61K 31/711*   (2006.01)
*A61K 38/00*    (2006.01)

(52) U.S. Cl. .................. 424/93.1; 536/28.2; 514/45
(58) Field of Classification Search .................. None
See application file for complete search history.

(56) References Cited

U.S. PATENT DOCUMENTS

| | | |
|---|---|---|
| 6,162,600 A | 12/2000 | Mayr et al. |
| 6,685,950 B2 | 2/2004 | Weber et al. |
| 6,805,870 B1 | 10/2004 | Mayr |
| 2006/0008471 A1 | 1/2006 | Weber et al. |

FOREIGN PATENT DOCUMENTS

| | | |
|---|---|---|
| DE | 44 05 841 | 1/1995 |
| DE | 199 22 407 | 11/2000 |
| JP | 9504803 | 5/1997 |

OTHER PUBLICATIONS

Weber et al. J. Gene Virol. Jan. 2003, vol. 84, pp. 1843-1852.*
Greg Folker, NIH News Releases 1998, p. 1.*
Perrin et al. 7th Conf Retrovir Oppor Infect Jan. 30 Feb. 2, 2000 Conf Retrovir Oppor Infect 7th 2000 San Franc Calif. Jan. 30, 2000-Feb. 2; 7: 179 , abstract No. 552, p. 1-2.*
Wong et al. UCSD Treatment Center News, Jan. 2000, pp. 1-8.*
Emery et al., Journal of Infectious Disease (2000) 182:428-434.
Garcia et al., AIDS (2001) 15(9):F29-F40.
"Infektionskrankheiten der Katze" published online Dec. 19, 2002, http://www.catdome.de/Krankheiten/infektionskrankheiten_der_katze.htm, retrieved on Oct. 26, 2005.
International Search Report for PCT/EP2005/007395, mailed on Nov. 24, 2005, 4 pages.
Letvin and Walker, Nature Medicine (2003) 9(7):861-866.
Lu et al., Nature Medicine (2003) 9:27-32.
Mayr, Microbiologica (2003) 26:7-12.
Mori et al., Journal of Virology (2000) 74:5747-5753.
Parienti, Expert Opinion Pharmacother. (2002) 3(6):719-726.
Powderly et al., JAMA (1998) 280:72-77.
Richards et al., Ann. NY Acad. Sci. (2002) 975:91-100.
Silvestri and Feinberg, Immunology of Infectious Diseases (2002) 30:453-477.
Weber et al., Journal of General Virology (2003) 84:1843-1852.
Non-Final Office Action for U.S. Appl. No. 09/903,013, mailed Dec. 16, 2002, 8 pages.
Notice of Allowance for U.S. Appl. No. 09/903,013, mailed Aug. 7, 2003, 7 pages.
Response to Restriction Requirement for U.S. Appl. No. 09/903,013, filed Oct. 17, 2002, 1 page.
Response to Non-Final Office Action for U.S. Appl. No. 09/903,013, filed Jun. 19, 2003, 5 pages.
Restriction Requirement for U.S. Appl. No. 09/903,013, mailed Sep. 12, 2002, 7 pages.

* cited by examiner

*Primary Examiner* — Bao Li
(74) *Attorney, Agent, or Firm* — Morrison & Foerster LLP

(57) ABSTRACT

The present invention relates to the use of *Parapoxviruses* in combination with other agents for the treatment of viral diseases, and in particular HIV infections and AIDS. The invention also relates to methods for producing medicaments based on combinations of *Parapoxviruses* and other antiviral agents, and to such medicaments. In particular, the invention relates to the use of *Parapoxviruses* in combination with agents of the kind used for antiretroviral therapy and highly active antiretroviral therapy (HAART).

14 Claims, 6 Drawing Sheets

PARAPOXVIRUSES IN COMBINATION WITH OTHER ANTIVIRAL AGENTS FOR THE TREATMENT OF VIRAL DISEASES

CROSS-REFERENCE TO RELATED APPLICATIONS

This application is a continuation of co-pending international patent application PCT/EP 2005/007395 filed on Jul. 8, 2005 and designating the U.S., and claims priority of European patent application EP 04 016 414.7 filed on Jul. 13, 2004. The contents of the above-referenced applications are incorporated herein by this reference in their entireties.

BACKGROUND OF THE INVENTION

Field of the Invention

The present invention relates to the use of *Parapoxviruses* in combination with other agents for the treatment of viral diseases, and in particular HIV infections and AIDS. The invention also relates to methods for producing medicaments based on combinations of *Parapoxviruses* and other antiviral agents. In particular, the invention relates to the use of *Parapoxviruses* in combination with agents of the kind used for antiretroviral therapy (ART) and highly active antiretroviral therapy (HAART).

The use of PPVO for the treatment of viral infections is known. Weber, O., et al., "Inactivated *Parapoxvirus ovis* (Orf Virus) Has Antiviral Activity Against Hepatitis B Virus And Herpes Simplex Virus," *J. Gen. Virol.* (2003) 84:1843-1852. The use of PPVO for enhancing the immune system is also known. Mayr, A., Development of a Non-Immunising, Paraspecific Vaccine From Attenuated Pox Viruses: A New Type of Vaccine," *New Microbiol.* (2003)26:7-12.

HAART is a known therapeutic procedure for reducing the viral load of HIV infections (HI viral load). It is also known that HAART produces an increase in the patients' CD4+ cells. Powderly, W., et al., "Recovery of the Immune System With Antiretroviral Therapy—The End of Opportunism?", *JAMA* (1998) 280:72-77. Those skilled in the art are aware that HAART does not, however, result in the elimination of the virus and the infection persists with a reduced viral load. It is also known that HAART does not elicit the permanent reconstitution of the immune system. Parienti, J., "Cytokine Therapy or Structured Treatment Interruptions in HIV Infection: Which is Best?," *Expert Opin. Pharmacother.* (2002) 3:719-726. If the therapy is terminated or interrupted the viral load rises again and the number of CD4+ cells falls. Garcia, F., et al., "The Virological and Immunological Consequences of Structured Treatment Interruptions in chronic HIV-1 Infection," *AIDS* (2001) 15:F29-40.

A combination of HAART and cytokines (such as IL-2) strengthens the immune system in HAART patients, although permanent reconstitution of the immune system is not elicited and side-effects occur. Emery, S., et al., "Pooled Analysis of 3 Randomized, Controlled Trials of Interleukin-2 Therapy in Adult Human Immunodeficiency Virus Type 1 Disease," *J. Infect. Dis.* (2000) 182:428-434.

Other types of therapy (e.g., the re-infusion of autologous, ex vivo expanded or modified HIV-specific CTL (cytotoxic T-lymphocyte) clones) increase the CD8+ cell response. This increase is however also only transient. Silvestri, G. and Feinberg, M., "Immune Intervention in AIDS," *Immunology of Infectious Diseases*, eds: Kaufmann, S. H. E.; Sher A.; Ahmend, R., ASM Press, Washington, D.C. (2002) Chapter 30:453-477. The precise cause of immunodeficiency and the correlates of the immune protection from HIV have not so far been elucidated. Letvin, N. L., et al., "Immunopathogenesis and Immunotherapy in AIDS Virus Infections," *Nat. Med.* (2003) 9:861-866. If the HI virus load is reduced by antiviral treatment at an early stage during the primary infection, effective immunity specifically against the immune deficiency virus can be established. Mori, K., et al", Suppression of Acute Viremia by Short-Term Postexposure Prophylaxis of Simian/Human Immunodeficiency Virus SHIV-RT-Infected Monkeys With a Novel Reverse Transcriptase Inhibitor (GW420867) Allows for Development of Potent Antiviral Immune Responses Resulting in Efficient Containment of Infection," *J. Virol.* (2000) 74:5747-5753. By contrast, no enhancement of the HIV-specific immune response occurs in chronically infected patients treated with HAART. Quite the contrary, the HIV-specific immune response is even reduced. Letvin, N. L. and B. Walker, Immunopathogenesis and Immunotherapy in AIDS Virus Infections," *Nat. Med.* (2003) 9:861-866. Experiments by Lu, W., et al. indicate that the defect in the immune control could lie in the induction phase of the immune response, i.e., in the initiation of a virus-specific response by dendritic cells. Lu, W., et al., "Therapeutic Dendritic-Cell Vaccine for Simian AIDS," *Nat. Med.* (2003) 9:27-32. These authors succeeded in demonstrating that SIV-infected Rhesus monkeys display a specific cellular and humoral immune response after the adaptive transfer of autologous dendritic cells loaded with inactivated HIV particles.

As is clear from the abovementioned prior art, no therapeutic method has so far been disclosed which not only reduces the viral load in chronically infected patients but also simultaneously elicits the permanent reconstitution of the immune systems of infected patients.

SUMMARY OF THE INVENTION

The present invention is therefore based on the technical problem of providing a therapeutic method which not only reduces the viral load of patients but also provides for the permanent reconstitution of the immune system. This therapeutic method should also have few or no undesirable side-effects.

The present invention is furthermore based on the technical problem of providing medicaments for use in a therapeutic method according to the invention.

Accordingly, these problems are solved by the use of a *Parapoxvirus* in combination with at least one additional antiviral agent for the preparation of a medicament for treating a viral disease.

Therefore, one object of the present invention is a method of producing a medicament for treating a viral disease, comprising the following steps: (1) providing *Parapoxvirus* in a therapeutically effective amount, (2) providing at east one additional antiviral agent in a therapeutically effective amount, (3) combining said amount of *Parapoxvirus* and said amount of additional antiviral agent to obtain a combination, and (4) formulating said combination into a pharmaceutically acceptable excipient.

Another object of the present invention is a medicament comprising *Parapoxvirus* in a therapeutically effective amount, at least one additional antiviral agent in a therapeutically effective amount, and a pharmaceutically acceptable excipient.

Another object is a method of treating a patient afflicted with a viral disease, comprising the following steps: (1) providing a combination comprising *Parapoxvirus* in a therapeutically effective amount, and at least one additional antiviral agent in a therapeutically effective amount, (2) administering said combination to the patient, and (3) repetition of steps (1) and (2), if required.

According to the invention a *Parapoxvirus* is understood to be a virus from the *Parapoxvirus* family, preferably *Parapoxvirus ovis, Parapoxvirus ovis* strain D1701, *Parapoxvirus ovis* strain NZ-2, *Parapoxvirus ovis* strain NZ-7, *Parapoxvirus ovis* strain NZ-10 or an orf virus (e.g., orf-11).

The invention also relates to the use of derivatives of the abovementioned *Parapoxvirus* strains obtained by passaging or adaptation using suitable cell systems such as for example human cells such as WI 38, MRC-5, monkey cells, e.g., Vero cells, bovine cells, such as, for example, BK-K13A47/Reg or MDBK, and bovine cells such as MDOK, in combination with substances which are effective in ART and/or HAART, for the production of medicaments against viral infections in humans and animals.

In addition, the invention relates to the use of parts or fragments of the abovementioned strains and their passaging and adaptation variants in combination with substances which are effective in ART and/or HAART. According to the invention, parts or fragments of a virus are understood to be genomic or subgenomic fragments of the whole virus, or of its genomic nucleic acid, or other components of the virus, which are expressed by means of suitable vectors such as Vaccinia viruses in suitable systems such as fibroblast cell cultures. In a preferred variant the parts or fragments of the *Parapoxvirus* according to the invention are purified by conventional methods, such as for example by filtration or chromatography. In another preferred variant the parts or fragments of the *Parapoxvirus* according to the invention are produced by recombination by methods known to the skilled man.

According to the invention, viral diseases are all human and animal diseases which are produced by infection with viruses or which are associated with infections with viruses.

In a preferred variant of the invention the antiviral agent is an antiretroviral agent.

In a preferred variant of the invention the viral disease is an HIV infection and/or AIDS.

According to the present invention the *Parapoxvirus* is preferably a *Parapoxvirus ovis, Parapoxvirus ovis* strain D1701, *Parapoxvirus ovis* strain NZ2, *Parapoxvirus ovis, Parapoxvirus ovis* strain NZ-7, *Parapoxvirus ovis* strain NZ-10 or *Parapoxvirus ovis* strain orf-11. In a further variant of the invention the *Parapoxvirus* is a *Parapoxvirus* obtained by the passaging of these strains.

It is preferred, if the *Parapoxvirus* is present in an inactivated form. The inactivation of the *Parapoxvirus* is carried out by virus inactivation methods known to the skilled man. In a preferred variant the *Parapoxvirus* is inactivated by the method described in European Patent No. EP-B1-0 312 839, the content of which is incorporated herein by reference.

The treatment of the viral disease according to the invention produces preferably a reduction in the viral load of patients. According to the invention, the reduction in the viral load is understood to be in particular a reduction in the number of virus particles in patients' bodies.

The treatment of the viral disease according to the invention elicits preferably the reconstitution of the immune system. According to the invention, the reconstitution of the immune system is characterized by an increase in the concentration of the CD3+ and CD4+ cells in the blood. In a preferred aspect of the invention, the reconstitution of the immune system is characterized by an increase in the concentration of the CD4+ and CD8+ cells in the blood. In another preferred aspect of the invention, the reconstitution of the immune system is characterized by an increase in the concentration of the CD4+ and CD8+ and CD3+ cells in the blood. In another preferred aspect of the invention the immune system is permanently, i.e., durably, reconstituted.

The treatment of the viral disease according to the invention produces preferably an increase in the CD4+ and/or CD8+ cells in the blood of the patient. The simultaneous increase in the concentration of the CD4+ and CD8+ cells in the blood is particularly preferred.

According to the invention the antiviral agent is preferably an agent for HAART therapy and/or an agent for ART therapy.

According to the present invention the antiviral agent comprises preferably Viread® (tenofovir disproxil fumarate, TDF) from Gilead Sciences, Emtriva™ (emtricitabine, FTC) from Gilead Sciences, Videx® and Videx® EC (didanosine, ddI) from Bristol-Myers Squibb, Zerit® and Zerit®XR (stavudine, d4T) from Bristol-Myers Squibb, Epivir® (lamivudine, 3TC) from GlaxoSmithKline, Retrovirr® (zidovudine, AZT) from GlaxoSmithKline, Ziagen® (abacavir, ABC) from GlaxoSmithKline, Combivir® (AZT and 3TC) from GlaxoSmithKline, Trizivir® (AZT, 3TC and ABC) from GlaxoSmithKline, Hivid® (zalcitabine, ddC) from Roche Laboratories, Sustiva® (efavirenz, EFV) from Bristol-Myers Squibb, Viramune® (nevirapine, NVP) from Boehringer Ingelheim, Rescriptor® (delavirdine, DLV) from Agouron Pharmaceuticals, Reyataz™ (atazanavir, ATV) from Bristol-Myers Squibb, Norvir® (ritonavir, RTV) from Abbott Laboratories, Agenerase® (amprenavir, APV) from GlaxoSmithKline, Kaletra® (Lopinavir/ritonavir, LPV/RTV) from Abbott Laboratories, Viracept® (nelfinavir, NFV) from Agouron Pharmaceuticals, Crixivan® (indinavir, IDV) from Merck&Co., Fortovase® (saquinavir, SQV-SGC) from Roche Laboratories, Invirase® (saquinavir mesylate, SQV-HGC) from Roche Laboratories, Fuzeon™ (enfuvirtide, T-20) from Roche Laboratories, Remune from The Immune Response Corp., Etravirine (TMC-125, R-165335) from Janssen Research Foundation Worldwide, Capravirine from Shionogi&Co. Ltd., UK-427857 from Pfizer or Tenofovir (PMPA) from Gilead Sciences or another antiviral or immunomodulating medicament as an active component.

It is especially preferred, if the antiviral agent comprises AZT, or 3TC, or PMPA as an active component.

The treatment of the disease according to the invention produces preferably the maturation and/or stimulation of the dendritic cells or other antigen-presenting cells.

The medicament or pharmaceutical composition, respectively, of the present invention may be administered in oral forms, such as, without limitation normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well-known to those of ordinary skill in the pharmaceutical arts. The medicament or pharmaceutical composition, respectively, of the present invention can be administered in intranasal form via topical use of suitable intranasal vehicles, or via transdermal routes, using transdermal delivery systems well-known to those of ordinary skilled in the art.

The dosage regimen with the use of the medicaments or pharmaceutical compositions, respectively, of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed.

The medicaments or pharmaceutical compositions, respectively, of the present invention are preferably formulated prior to administration and include one or more pharmaceutically acceptable excipients. Excipients are inert substances such as, without limitation carriers, diluents, flavoring agents, sweeteners, lubricants, solubilizers, suspending agents, binders, tablet disintegrating agents and encapsulating material.

The medicament or pharmaceutical formulation, respectively, of the present invention preferably comprises one or more pharmaceutically-acceptable excipients that are compatible with the other ingredients of the formulation and not deleterious to the recipient thereof. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills, powders, lozenges, elixirs, suspensions, emulsions, solutions, syrups, aerosols, ointments, containing, for example, up to 10% by weight of the active pharmaceutical composition, soft and hard gelatine capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, a optionally, disintegrating agents, such as, without limitation, maize, starch, methyl cellulose, agar bentonite, xanthan gum, alginic acid, and the like; and optionally, binding agents, for example, without limitation, gelatin, polygeline, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxy methyl cellulose, low melting waxes, and cocoa butter. Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active pharmaceutical composition of the present invention, calculated to produce the desired therapeutic effect, in association with one or more excipients. Dosages will vary from about $10^3$ to about $10^{12}$ physical number of viral particles per application or will be based on physical number of particles/kg/day.

The medicaments or pharmaceutical compositions, respectively, of the present invention may be administered in a single daily dose, or the total daily dose may be administered in divided doses, two, three, or more times per day. Where delivery is via transdermal forms, of course, administration is preferably continuous.

DESCRIPTION OF PREFERRED EMBODIMENTS

Example 1

PPVO Induces Maturation of Dendritic Cells In Vitro

Figure 1:
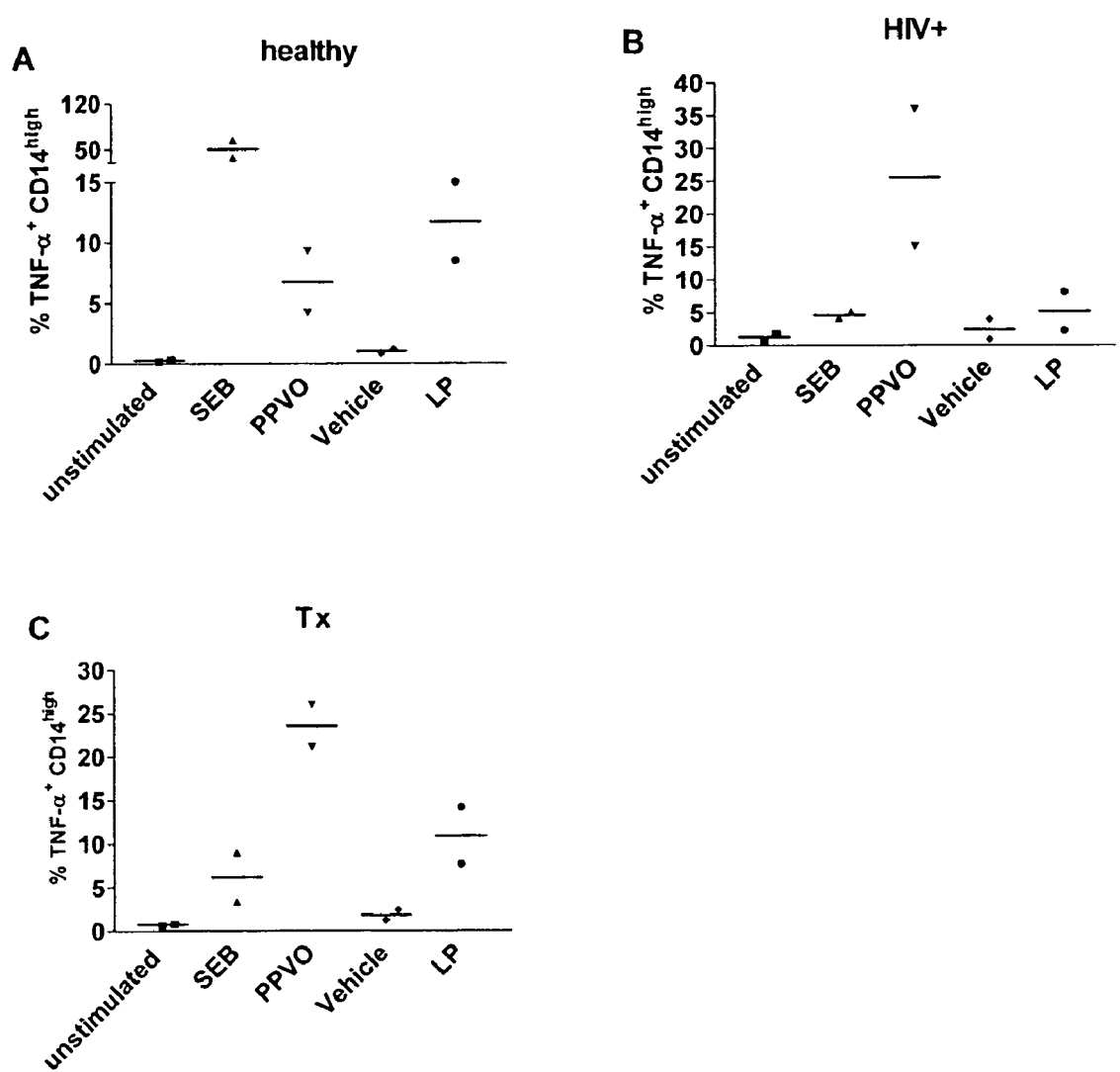
FIG. 1—TNF-α production of $CD14^{high}$ monocytes of healthy or immunocompromised donors after stimulation with PPVO. Whole blood of two donors in each case was analysed. Blood of (A) healthy donors, (B) HIV-infected donors (HIV+) or (C) transplantation patients (Tx) was incubated for 6 hours with Staphylococcus Enterotoxin B (SEB; 2.5 µg/ml), PPVO ($6 \times 10^8$ viral particles), vehicle as placebo control for PPVO, or lipopeptide (LP 1 µg/ml). Subsequently the relative amount (in %) of TNF-α producing $CD14^{high}$ monocytes was determined by FACS analysis.

Dendritic cells are antigen-presenting cells that play a major role in initiating primary immune responses. Their phenotypic and functional characteristics are intimately linked to their stage of maturation. Richards, J., et al., Integrated Genomic and Proteomic Analysis of Signaling Pathways in Dendritic Cell Differentiation and Maturation," Ann. N.Y. Acad. Sci. (2002) 975:91-100. Stimulation of whole blood cells with PPVO leads to maturation of DCs thereby converting them to a functional status where they are able to induce immune responses very efficiently: PPVO is able to stimulate TNF-α expression in $CD14^{high}$ monocytes (FIG. 1) as well as in immature DCs. TNF-α production in $CD14^{high}$ monocytes from whole blood samples is not restricted to healthy donors but PPVO stimulates TNF-α expression also in $CD14^{high}$ monocytes from immunosuppressed HIV patients as well as transplantation patients (FIG. 1). In addition stimulation of whole blood with PPVO for 24 hrs leads to the activation of T-cells (CD4+ and CD8+) as seen by the expression of the early activation marker CD69 in blood from healthy and immunocompromised donors (data not shown). Therefore, in immunosuppressed and in particular in HIV infected patients the early steps of immune response seem to be influenceable by PPVO.

Example 2

HIV IN HU-PBL-SCID

Figure 2:
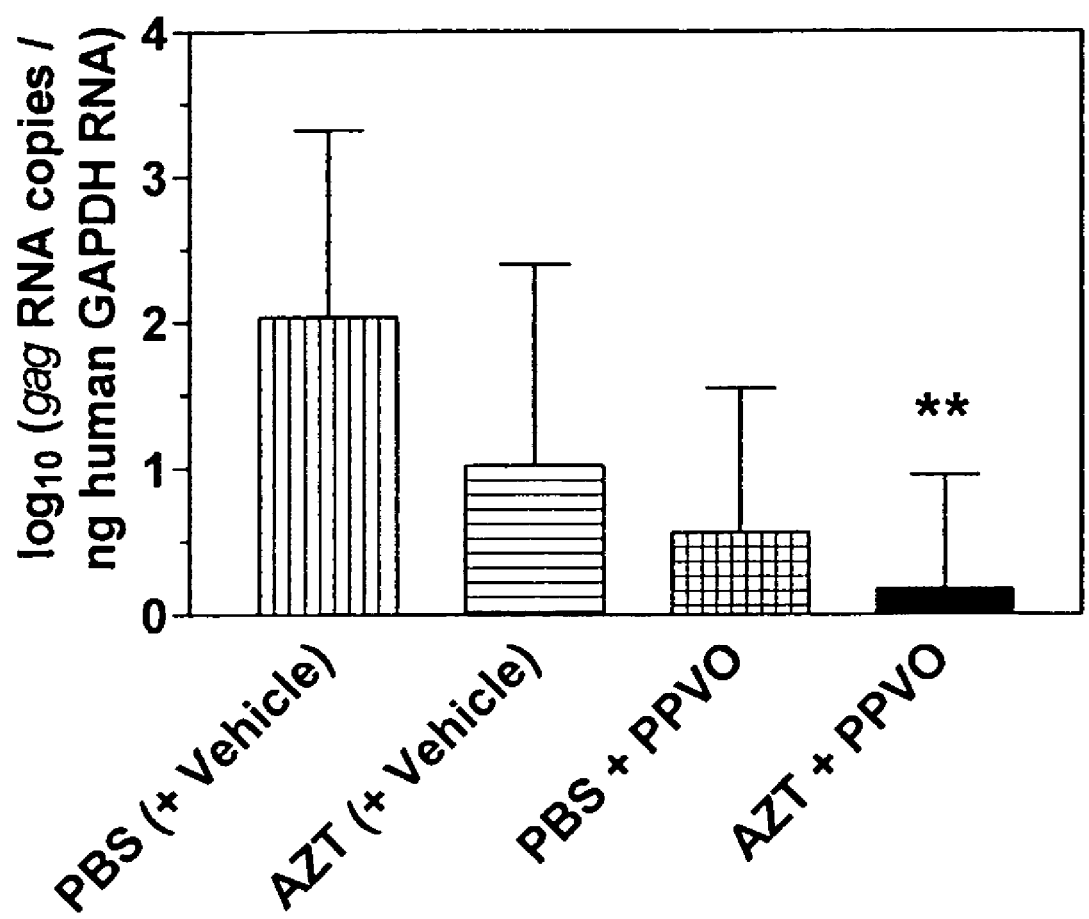
FIG. 2—PPVO treatment reduces HIV viral load in hu-PBL-SCID mice. HIV copy number (normalized to human GAPDH RNA) in spleen from hu-PBL-SCID mice infected with $HIV_{Bal.}$ Shown are the means of each treatment group±standard error. PBS (+Vehicle) n=13, AZT (+Vehicle) n=17, PBS+PPVO n=15, AZT+PPVO n=19. **Viral load is significantly reduced in the AZT+PPVO treatment group compared to PBS (+Vehicle) (p<0.01). Data derived from two separate experiments, Vehicle was used only in one experiment.

To test the activity of PPVO against HIV the immune modulator was investigated in the hu-PBL-SCID Model. Briefly, SCID mice were transplanted with human PBMC's. Animals with confirmed reconstitution were selected and infected with $HIV_{Bal}$ by intraperitoneal injection. Treatment was initiated 30 minutes after infection. AZT (100 mg/kg/day) was given twice a day orally whereas PPVO was given only twice weekly by i. p. route. One dose of PPVO consisted of $2 \times 10^4$ antigen units measured by ELISA. Placebos (pyrogenfree PBS and vehicle control) were used following the respective treatment schedules. Mice were sacrificed in the third week after HIV infection. Viral load was monitored in RNA extracted from spleen tissue. Compared to placebo (PBS+Vehicle) PPVO treatment could be demonstrated to reduce HIV viral load. Addition of PPVO to standard antiretroviral therapy (AZT) led to even better inhibition of HIV replication—viral load was reduced significantly ($p<0.01$, Kruskal-Wallis test) by ca. 90% (FIG. 2).

Example 3

SIV

The hu-PBL-SCID mice represented the acute phase of HIV infection. Usually, treatment of HIV infected persons starts later in the course of infection. In order to examine the efficacy of PPVO in a clinically more relevant setting the SIV (simian immunodeficiency virus, simian homologue to HIV) infection model was employed.

Fourteen rhesus monkeys were infected with SIV. The first treatment interval was initiated after viremia at the beginning of the chronic phase at eight weeks post infection (p. i.) for nine weeks. Four animals were treated with antiretroviral therapy (ART), four were treated with PPVO and four were treated with both, ART and PPVO. Two animals were placebo treated and served as controls. ART treatment was given daily subcutaneously whereas PPVO treatment was given only twice a week by intramuscular injection. A second and a third 8-week treatment interval was initiated at week 22 and 51 p. i., respectively, with intraveneous application of PPVO.

Figure 3:
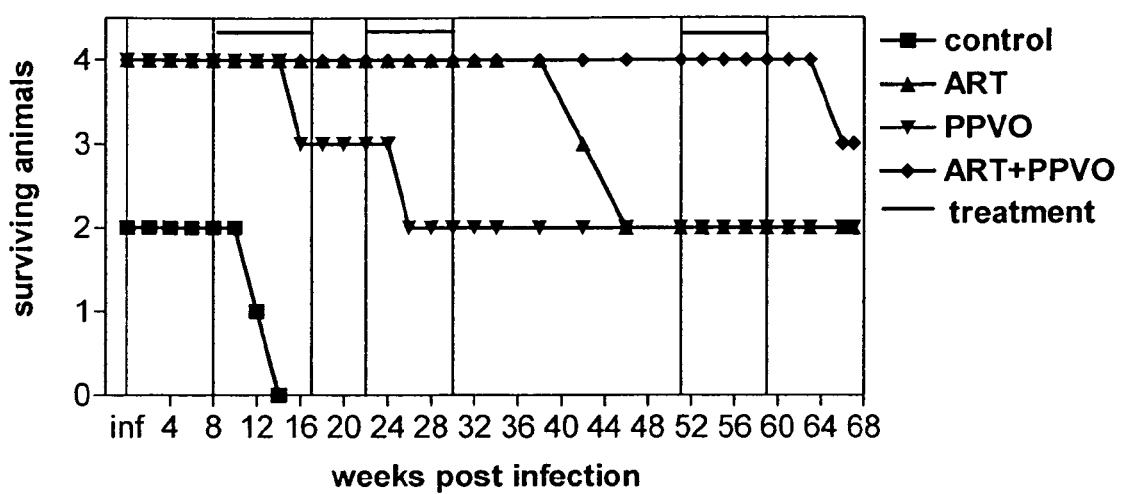
FIG. 3—PPVO in combination with ART leads to longer survival of SIV infected macaques. Shown is the number of surviving animals in the course of the experiment. PPVO+ART leads to a decrease of mortality and an extended life span compared to all other groups. All deceased animals died from syndromes linked to immunodeficiency.
Figure 4:
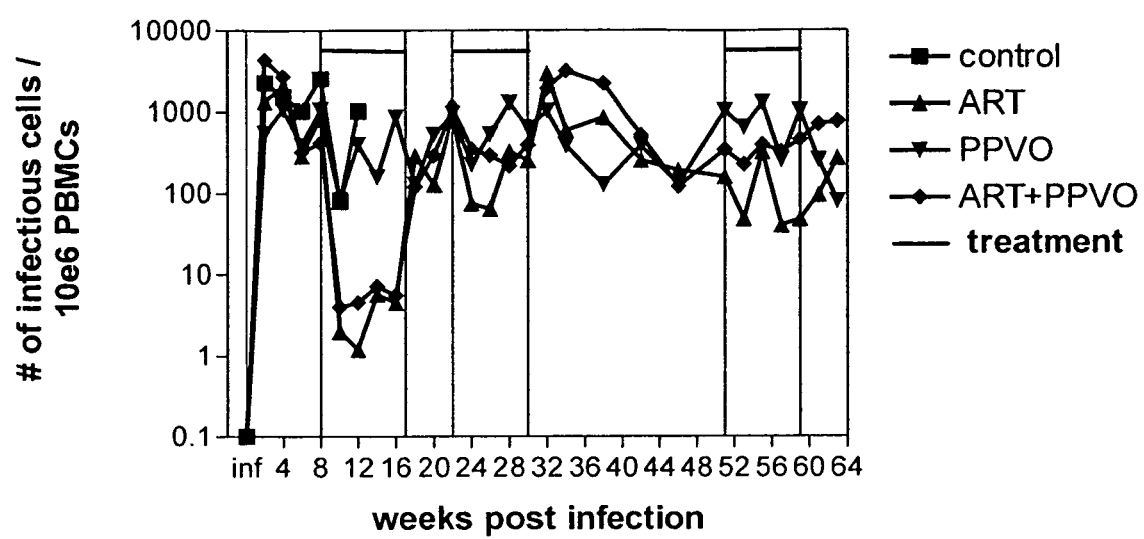
FIG. 4—ART but not PPVO leads to reduction in SIV viral load. Shown is cell bound viral load which correlates with SIV plasma viral load. Given are the means of each group (n=2-4). Fast viral rebound could be observed in the ART as well as in the ART+PPVO group.
Figure 5A:
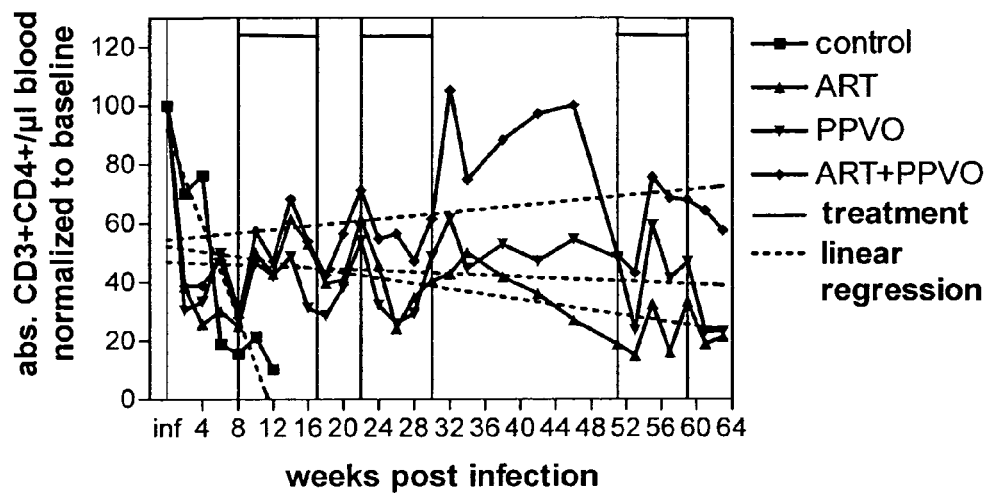
FIG. 5A—PPVO treatment leads to regain of CD4+ cells in SIV infected monkeys. Given are the means of each group for absolute number of CD3+CD4+ cells/µl blood in % of baseline at indicated time points (n=2 to 4 animals). PPVO leads to a stabilization or even an increase in CD3+CD4+ cell number whereas animals in the ART alone group experience CD3+CD4+ cell loss.
Figure 5B:
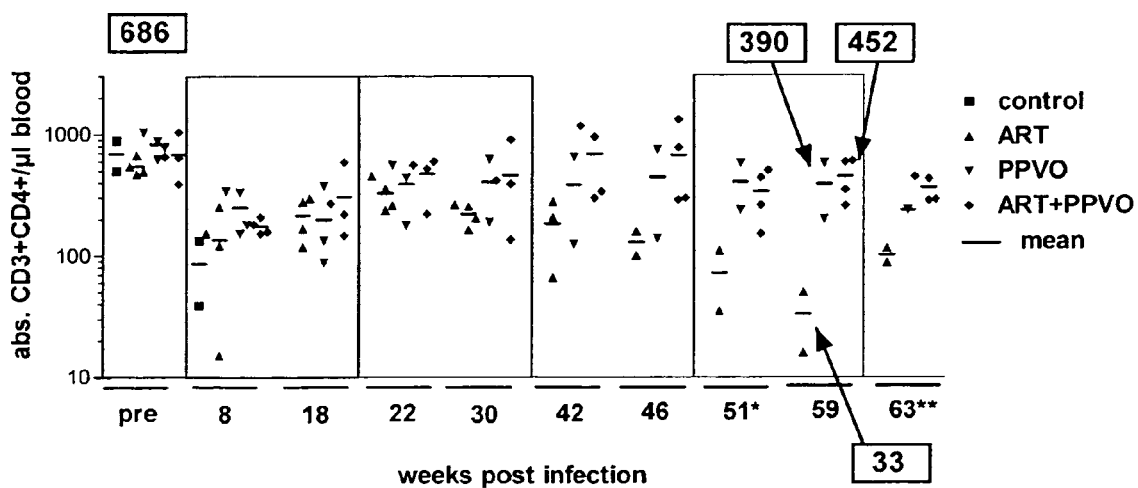
FIG. 5B—PPVO treatment leads to regain of CD4+ cells in SIV infected monkeys. Given is the individual absolute number of CD3+CD4+ cells/µl blood at indicated time points with the mean per group. Numbers in colored boxes represent the mean absolute number of CD3+CD4+ cells/µl blood of all groups at time pre infection or the mean absolute number of CD3+CD4+ cells/µl blood for each group at week 59 p. i., respectively; ☐ treatment interval; *ART: week 53 p. i.; **PPVO: value of one animal missing. PPVO treatment leads to stabilization or even an increase in CD3+CD4+ cell number whereas animals in the ART alone group experience CD3+CD4+ cell loss (until shortly after treatment, e.g., week 63).

No toxicity of PPVO was observed during the whole experiment. The number of surviving animals is increased and their lifespan is extended in PPVO plus ART treated compared to animals treated with ART or PPVO alone (FIG. 3). This is not due to ART as a decrease in viral load was observed in both groups treated with ART but life span extension is only seen in the PPVO+ART group (FIG. 4). As shown in FIGS. 5A and 5B PPVO treatment leads to regain of CD4+ cell count, in the ART plus PPVO as well as in the PPVO alone group (mean at week 59 p. i.: 452 or 390 CD3+CD4+ cells/µl blood, respectively) whereas ART alone treatment results in continuous loss of CD4+ cells (mean at week 59 p. i.: 33 CD3+CD4+ cells/µl blood) (FIGS. 5A and 5B).

Figure 6:
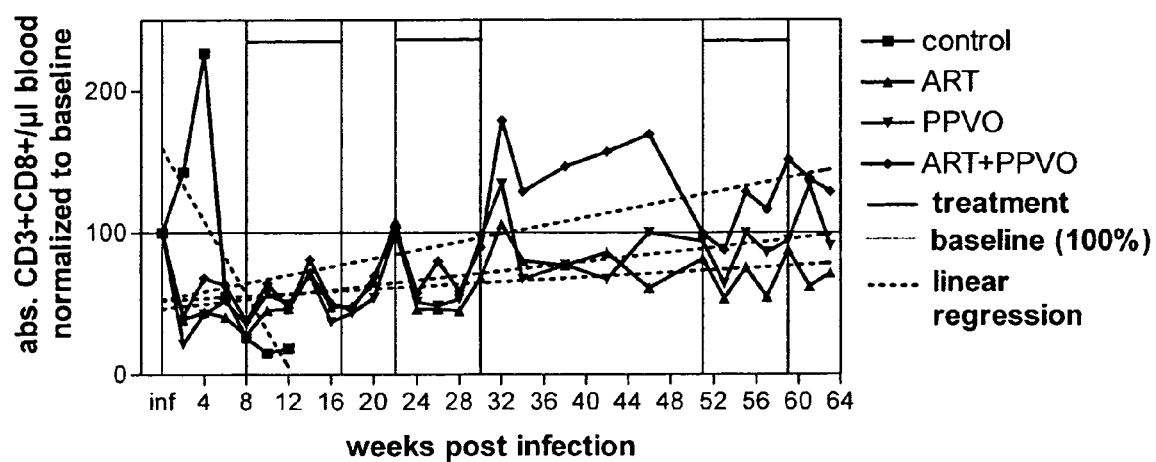
FIG. 6—PPVO treatment leads to increase in CD3+CD8+ cell number above baseline. Given is the individual absolute number of CD3+CD8+ cells/µl blood in % of baseline at indicated time points (n=2 to 4 animals). PPVO+ART is exceeding the baseline value and is more effective in increasing CD3+CD8+ cells than PPVO alone.

PPVO leads to an increase in CD8+ cells, even more effectively when combined with ART (FIG. 6). ART alone does not lead to higher CD8+ cell count. CD4+/CD8+ ratio is slowly decreasing in nearly all animals (data not shown).

Even if viral load could not be reduced in this hard to treat model of SIV disease these are very intriguing results. As seen by the increase in CD4+ and CD8+ cells PPVO enhances the T cell response in these chronically infected animals. Immune defense against pathogens seems to be enhanced as extrapolated from the extended life span and higher number of surviving animals in the ART+PPVO treatment group.

Therefore, what is claimed, is:

1. A method of producing a medicament for treating a viral disease, comprising the following steps:
    (1) Providing *Parapoxvirus ovis* strain NZ2 in a therapeutically effective amount,
    (2) Providing at least one additional antiviral agent in a therapeutically effective amount,
    (3) Combining said amount of *Parapoxvirus* and said amount of additional antiviral agent to obtain a combination, and
    (4) Formulating said combination into a pharmaceutically acceptable excipient,
    wherein said viral disease is an HIV infection and/or AIDS, and wherein said at least one additional antiviral agent is selected from the group consisting of: an agent for Highly Active Antiretroviral Therapy (HAART), zidovudine (AZT), lamivudine (3TC), and Tenofovir (PMPA).

2. Method according to claim 1, wherein said *Parapoxvirus* is present in inactivated form.

3. Method according to claim 1, wherein said at least one additional antiviral agent is an antiretroviral agent.

4. Method according to claim 1, wherein said at least one additional antiviral agent is an agent for HAART therapy.

5. Method according to claim 1, wherein said at least one additional antiviral agent is AZT.

6. Method according to claim 1, wherein said at least one additional antiviral agent is 3TC.

7. Method according to claim 1, wherein said at least one additional antiviral agent is PMPA.

8. A method of treating a patient afflicted with a viral disease, comprising the following steps:
(1) providing a combination comprising *Parapoxvirus ovis* strain NZ2 in a therapeutically effective amount, and at least one additional antiviral agent in a therapeutically effective amount,
(2) Formulating said combination into a pharmaceutically acceptable excipient,
(3) Administering said combination to the patient, and
(4) Repetition of steps (1) to (3), if required,
wherein said viral disease is an HIV infection and/or AIDS, and wherein said at least one additional antiviral agent is selected from the group consisting of: an agent for HAART, AZT, 3TC, and PMPA.

9. Method according to claim 8, wherein said *Parapoxvirus* is present in inactivated form.

10. Method according to claim 8, wherein said at least one additional antiviral agent is an antiretroviral agent.

11. Method according to claim 8, wherein said at least one additional antiviral agent is an agent for HAART therapy.

12. Method according to claim 8, wherein said treatment results in a reduction of the viral load of patients.

13. Method according to claim 8, wherein said treatment elicits the reconstitution of the immune system of the patient.

14. Method according to claim 8, wherein said treatment elicits an increase in the CD4+ and/or CD8+ cells in the patient.

* * * * *